(12) United States Patent
Krishnamurthy

(10) Patent No.: US 6,558,946 B1
(45) Date of Patent: May 6, 2003

(54) AUTOMATED SAMPLE PROCESSING FOR IDENTIFICATION OF MICROORGANISMS AND PROTEINS

(75) Inventor: Thaiyalnayaki Krishnamurthy, Ellicott City, MD (US)

(73) Assignee: The United States of America as represented by the Secretary of the Army, Washington, DC (US)

(*) Notice: Subject to any disclaimer, the term of this patent is extended or adjusted under 35 U.S.C. 154(b) by 0 days.

(21) Appl. No.: 09/940,906

(22) Filed: Aug. 28, 2001

Related U.S. Application Data (60) Provisional application No. 60/228,589, filed on Aug. 29, 2000.

(51) Int. Cl.[7] .................................................. C12M 1/34
(52) U.S. Cl. ...................... 435/288.6; 250/281; 250/287; 250/288; 210/198.2
(58) Field of Search ......................... 435/287.2, 288.6; 250/281, 287, 288; 210/198.2

(56) References Cited

U.S. PATENT DOCUMENTS 5,856,082 A * 1/1999 Aebersold et al.
6,177,266 B1   1/2001 Krishnamurthy ............ 435/173

* cited by examiner

*Primary Examiner*—David A. Redding
(74) *Attorney, Agent, or Firm*—Ulysses John Biffoni (57) ABSTRACT

The present invention concerns a method for rapidly identifying biological agents in a sample suspected of containing the same. The biomarkers are released from biological agents present in a sample, separated from contaminants present in the sample, ionized to form an ionized stream of biomarkers which are sent to a mass spectrometer to obtain a mass spectral profile of the biomarkers in the sample for analysis and identification. The present invention is also directed to an apparatus useful for carrying out the steps of the above method in an automated mode.

33 Claims, 4 Drawing Sheets

AUTOMATED SAMPLE PROCESSING FOR IDENTIFICATION OF MICROORGANISMS AND PROTEINS

RELATED APPLICATION

The present Application claims the priority of U.S. Provisional Application Serial No. 60/228,589 filed Aug. 29, 2000, which is fully incorporated herein by reference.

GOVERNMENT INTEREST

The invention described herein may be manufactured, licensed, and used by or for the U.S. Government.

FIELD OF THE INVENTION

The present invention relates to biomarkers, more particularly to methods and apparatus for rapidly identifying biological agents through the automated detection of biomarkers such as proteins released from extracts or whole intact biological agents that may be present in an environmental or biological sample.

BACKGROUND OF THE INVENTION

Rapid and accurate identification of biological agents is essential in diagnosing diseases, anticipating epidemic outbreaks, monitoring food supplies for contamination, regulating bioprocessing operations, and detecting threats of warfare. It is highly desirable not only to rapidly distinguish between related biological agents especially pathogenic agents, but also to unmistakably identify species and strains in complex matrices especially for the purpose of risk assessment in field situations.

The classification of biological agents such as bacteria and viruses has traditionally been based on biochemical and morphological tests. Recently, several analytical techniques have been developed which enhance the speed and accuracy of the identification of such biological agents. In these techniques, the biochemical components of biological agents are examined to determine chemotaxonomic markers, which are specific for each species. The chemotaxonomic markers, or biomarkers, may include any one or a combination of the classes of molecules present in the cells such as lipids, phospholipids, lipopolysaccharides, oligosaccharides, proteins, DNA, and the like.

Recently, mass spectrometric techniques have been developed for generating specific protein profiles for various biological agents. These techniques generally employ electrospray ionization (ESI) or matrix-assisted laser desorption ionization (MALDI) of protein extracts followed by mass spectrometric (MS) or tandem mass spectrometric (MS/MS) analysis. ESI and MALDI are ionization techniques that have enabled dramatic progress to be made in performing mass spectrometry on large biomolecules including proteins. For example, the MALDI technique, combined with time-of-flight mass spectrometry (TOF-MS), has been used to differentiate biological agents using a crude protein extract.

The MALDI-MS technique is based on the discovery in the late 1980's that desorption/ionization of large, nonvolatile molecules such as proteins and the like can be made when a sample of such molecules is irradiated after being co-deposited with a large molar excess of an energy-absorbing "matrix" material, even though the molecule may not strongly absorb at the wavelength of the laser radiation. The abrupt energy absorption initiates a phase change in a microvolume of the absorbing sample from a solid to a gas while also inducing ionization of the molecule of the sample. The ionized molecules are accelerated toward a detector through a flight tube. Since all ions receive the same amount of energy, the time required for ions to travel the length of the flight tube is dependent on their mass. Thus low-mass ions have a shorter time of flight (TOF) than heavier molecules. Detailed descriptions of the MALDI-TOF-MS technique and its applications may be found in review articles written by E. J. Zaluzec et al. (*Protein Expression and Purification,* Vol. 6, pp. 109–23 (1995)) and D. J. Harvey (*Journal of Chromatography A,* Vol. 720, pp. 429–4446 (1996)), and in U.S. Pat. No. 6,177,266, each of which is incorporated herein by reference.

Aside from the means for desorption/ionization, the ESI-MS technique is similar to the MALDI-MS technique in principle. In ESI, a dilute solution of an analyte containing large, nonvolatile molecules such as proteins and the like is slowly supplied through a short length of capillary tubing. The capillary tubing is held at a few kilovolts with respect to the counter electrode, positioned about a centimeter away. The strong electric field at the end of the capillary tubing draws the solution into a cone-shaped form, and at the tip of the cone the solution is nebulized into small charged droplets. As the charged droplets travel towards the counter electrode, the solvent evaporates, thus ultimately yielding molecular ions. The ions are drawn into the vacuum chamber through a small aperture or another piece of capillary tubing, which is usually heated to ensure that the ions are completely desolvated. The molecular ions are then extracted into a mass spectrometer for analysis.

In both techniques, ionization is a critical event in mass spectrometry where the masses of the ionized particles can be accurately measured by the mass spectrometer. The mass spectrometer is a highly sensitive analysis instrument which provides the user with information on the molecular weight and structure of organic compounds and the like. Once the mass of the ion is known, the chemical composition and structure can further be determined through the use of tandem mass spectrometric techniques as known in the art. The utilization of ESI and MALDI when combined with mass spectrometry provides accurate analysis of large biological molecules such as proteins and DNA. The detection limits with mass spectrometry, especially MALDI, depend largely on concentrating the sample and reducing the volume thereof. Sensitivity will increase as ultramicro methods for concentrating and transferring ever smaller-volume samples are developed.

Typically, samples containing biomarkers released from intact biological agents can be directly subjected to mass spectrometric analysis using the above techniques. However, the presence of contaminants, ionizable impurities and non-polar detergents that may be present, undesirably suppresses ionization efficiency under the ESI and MALDI conditions. The removal of such contaminants substantially improves the sensitivity and thus improves the reliability of the identification of the biological agents while usefully extending the operating life of the MALDI and ESI equipment. Furthermore, during field use, the identification and detection of the biological agents, should be carried out in a continuous automated manner with little intervention by human personnel for efficient implementation and operation such as routine monitoring of suspected sites over extended periods of time.

Accordingly, there is a need to develop methods for rapidly identifying biological agents through the automated detection of biomarkers such as proteins released from extracts or whole intact biological agents that may be present in an environmental or biological sample. Such methods would permit protective measures or countermeasures to be quickly implemented in the event of, for example, an attack by weapons employing the same. There is also a need to provide an apparatus that performs the above-mentioned methods as a single operational system capable of routine field, hospital, bioprocessing and manufacturing, and clinical laboratory use.

It would also be desirable to optimize and improve the sensitivity and resolution of the detected ions using ESI-MS and MALDI-MS techniques, thus providing improved reliability in detection and identification. Still further, it would be desirable to provide detection and identification through protein sequencing for greater discrimination and sensitivity. Moreover, the demand for methods and apparatus capable of rapidly identifying biological agents has applications beyond those of the military such as in the pharmaceutical, medical, food and public safety industries, and the like.

SUMMARY OF THE INVENTION

The present invention is generally directed to methods for rapidly identifying biological agents through the automated detection of biomarkers preferably proteinaceous biomarkers released from extracts or whole intact biological agents that may be present in a sample suspected of containing the same, and to an apparatus for conducting the same. The apparatus of the present invention provides means for rapid and automated processing and identification of biological agents. Upon proper identification, a specific therapy or preventative measure may be implemented in response to the presence of the biological agent. The apparatus and methods may also be used to discover new biological agents.

In one aspect of the present invention, there is provided a method for rapidly identifying biological agents in a sample suspected of containing the same, the method comprises the steps of:
  releasing biomarkers from the biological agent present in the sample;
  separating and concentrating the biomarkers from contaminants which may be present in the sample;
  ionizing the biomarkers to form a stream of ionized biomarkers;
  directing the stream of the ionized biomarkers to a detector capable of analyzing the ionized biomarkers; and
  identifying the biological agent from the analyzed ionized biomarkers.

In another aspect of the present invention, there is provided an apparatus for rapidly identifying biological agents in a sample suspected of containing the same, the apparatus comprises:
  releasing means for releasing biomarkers from the biological agents in the sample;
  at least one sample processing module each fluidly connected to the releasing means, said at least one sample processing module each including a cleanup and concentration column for cleaning up the sample of contaminants and concentrating the volume of the sample;
  an ionization source fluidly connected to said at least one sample processing module, for ionizing the discrete biomarkers and forming a stream of ionized biomarkers;
  a detector for analyzing the stream of ionized biomarkers to obtain at least one parameter of the ionized biomarkers indicative of the identity of the biological agent; and
  a controller operatively connected to the releasing means, the sample processing module, the separation module, the ionization source and the detector to provide programmed coordination of said components for orderly passage of the sample through each.

BRIEF DESCRIPTION OF THE DRAWINGS

The following drawings are illustrative of embodiments of the invention and are not to be construed as limiting the invention as encompassed by the claims forming part of the application.

DETAILED DESCRIPTION OF THE INVENTION

The present invention is directed to methods and apparatus for rapidly identifying biological agents such as bacteria, viruses, and toxins that may be present in biological and environmental samples. The automated methods of the present invention provide a process for accurately identifying biological agents by identifying biomarkers, which are characteristic of the biological agent using conventional ionization mass spectrometric techniques. The present invention further provides for the separation of biomarkers from small quantities of biological agents, including infectious agents, to determine masses of intact biomarkers such as proteins, and for characterizing the biomarkers through mass spectrometry using electrospray ionization or matrix-assisted laser desorption ionization techniques. In another aspect of the present invention, protein-based biomarkers may be cleaved into peptide fragments through proteolytic digestion to characterize the peptide sequences or structures of the protein-based biomarkers through the use of tandem mass spectrometry in combination with ESI or MALDI techniques.

The use of mass spectrometric techniques described herein for identifying biological agents are related to techniques disclosed in Krishnamurthy et al., "Detection of Pathogenic and Non-Pathogenic Bacteria by Matrix-assisted Laser Desorption/Ionization Time-of-Flight Mass Spectrometry", *Rapid Communications in Mass Spectrometry*, Vol. 10, 883–88 (1996); Krishnamurthy et al: "Rapid Identification of Bacteria by Direct Matrix-assisted Laser Desorption/Ionization Mass Spectrometric Analysis of Whole Cells", *Rapid Communications in Mass Spectrometry*, Vol. 10, 1992–1996 (December 1996); Krishnamurthy et al; "Bacterial Detection by Mass Spectrometry", *Indian Society for Mass Spectrometry*, pp. 105–122 (November 1996); Krishnamurthy et al., "Liquid Chromatography/microspray Mass Spectrometry for Bacterial Investigations", *Rapid Communications in Mass Spectrometry*, 13: 39–49, 1998; Krishnamurthy et al. "Mass Spectral Investigations on Microorganisms," J. Toxicology-Toxin Reviews, 19, 95–117, 2000; and Krishnamurthy et al., "Automated Sample Processing for Mass Spectrometric Identification of Biological Agents," Proceedings of Joint Conference on Point Detection for Chemical and Biological Defense, 252–262, 2000, each of which is incorporated herein by reference.

In a particular aspect of the present invention the sample is rapidly processed and the contaminants efficiently and rapidly removed from the sample in a manner, which enables the apparatus to process more samples than by conventional methods. The method and apparatus of the present invention is adapted for providing rapid and accurate detection of a range of biological agents, in a system that is easy to employ and implement under various environmental conditions as required for military use, for example, under battlefield conditions.

By way of example, the invention will be described with reference to bacteria as a representative biological agent. It will be understood that the invention is also applicable to a wide range of biological agents including viruses, mycoplasmas, yeasts, oocysts, toxins, and other infectious and non-infectious microorganisms. The invention is especially suitable for the identification of infectious biological agents and protein toxins, and will be described in this context.

The term "biomarkers" as used herein refers to any one or a combination of classes of molecules present in cells such as lipids, phospholipids, lipopolysaccharides, oligosaccharides, proteins, DNA, and the like that are useful in the construction of the chemotaxonomic profile of the biological agent of interest for the purposes of the detection and identification. The term "chemotaxonomic profile" shall mean a system by which a chemical substance such as a biomarker can be used to identify a particular classes or species of a biological agent.

As noted above, the biological agent can be unambiguously identified through the detection of specific protein biomarkers. Direct MALDI-MS or liquid chromatographic/microspray-MS analysis of the intact bacterial proteins generated a mass spectral profile showing the protein biomarkers specific for the individual bacterium as well as identification of biological agents such as protein toxins from unknown samples. The genus, species, and strain specific biomarkers may be generated for pathogenic and non-pathogenic biological agents alike. These biomarkers provide distinguishing features between pathogenic and non-pathogenic bacteria. Samples containing multiple bacteria of differing genus, species, and strain, and/or protein toxins may also be distinguished by employing the present invention. The present invention may also be utilized for identifying biological agents of viral origins through the analysis of biomarkers such as capsid proteins found in the outer coating thereof. Although such disrupted samples of bacteria can be used for direct analysis through ESI-MS or MALDI-MS, rigorous clean up is preferable for obtaining accurate and unambiguous mass spectral profile readings of the biomarkers contained therein.

The present invention preferably utilizes mass spectrometric techniques including, but not limited to, matrix-assisted laser desorption ionization (MALDI) and electrospray ionization (ESI) incorporating techniques such as nanospray and microspray ionization to generate ionized biomolecules for analysis in a mass spectrometer. The mass spectrometer generates a unique mass spectral profile of the biomolecules including bacterial protein extracts that are present in the sample. These profiles contain biomarkers and effectively provide a means for distinguishing between bacteria of different genera, species, and strains. Comparable profiles are generated when the method or apparatus performs under different ESI or MALDI instruments. The invention is further explained by reference to the non-limiting examples set forth hereinafter.

The present invention includes a method for generating unique mass spectral profiles of individual biomarkers released from bacterial extract or whole bacterial cell suspensions. The mass spectral profiles reveal the molecular mass of each protein biomarkers to yield a unique pattern, which can be used to distinguish between bacteria of different genera, species and strain. The method of the present invention further is capable of identifying a bacterium regardless of whether it is in a vegetative or sporulated form. For practical utility, mass spectral analysis of bacterial samples should be robust, i.e., not affected by various contaminants, which may be present in the sample.

The present invention is further directed to a method of preparing and compiling a library of mass spectrometric profiles of known biological agents for the purpose of comparing mass spectral profiles of biological agents of unknown samples with the profiles compiled in the library to obtain positive matches resulting in reliable and accurate identification of the unknown biological agents. The method generally comprises releasing biomarkers from the known biological agents present in the sample, separating and concentrating the biomarkers from contaminants which may be present in the sample, ionizing and accelerating the biomarkers by an electric field to form a stream of ionized biomarkers, directing the stream of the ionized biomarkers to a detector capable of analyzing the ionized biomarkers, generating and storing a profile of the biomarkers from the known biological agent for compilation in a library, and repeating the above steps for other known biological agents.

The mass spectrometric library of profiles of biomarkers from known biological agents may be used for comparison with profiles of biomarkers from unknown biological agents. A match between the profiles of biomarkers from unknown biological agents with one from known biological agents would provide positive identification of the biological agent contained in the sample.

In practice, a biological (e.g. blood) or an environmental (e.g. water) sample suspected of containing a biological agent is suspended in a suitable solvent and ultrasonically disrupted to enhance the release of the biomarkers from the biological agent. The ultrasonically disrupted sample is centrifuged to separate particles having sedimentaton rates higher than that of the biomarkers to be analyzed. The sample is then filtered to remove the sediment, cellular debris, and other insoluble particulates present to yield a supernatant. The supernatant is then used as a sample for analysis as described herein. Mass spectrometric methods have now been described which allow accurate measurement of biomarkers up to at least 500,000 Daltons. Mass spectral profiles may then be generated, collected, and compared to spectral profiles of known protein extracts or whole cells of known bacteria to identify the unknown bacteria or biological agent present in a sample.

In order to work with intact protein molecules, the sample is preferably concentrated to a viable reduced volume in the absence of undesirable contaminants including salts, detergents, buffers, ionizable molecules, enzymes, surfactants, organic solvents, and the like which can interfere with the mass spectrometric detection and measurement. The removal of contaminants is accomplished by ultrafiltration, typically employing ultrafiltration beads in microcolumns and separation media including but not limited to, reverse phase, ion exchange sorbents, and chromatographic separation materials, and the like, which are useful for isolating the biomarkers from the contaminants according to particle size and/or charge. During the contaminant removal process, the sample may be simultaneously concentrated for obtaining optimal mass spectral results. Optionally, a liquid chromatography step for separating the components prior to introduction to the mass spectrometer may be included for improved mass measurement.

In another embodiment of the present invention, an apparatus is developed in which suspensions containing biological agents including bacteria and the like, are treated to release the biomarkers from the cellular constructs of the biological agents. The released biomarkers are concentrated and purified by ultrafiltration means to yield a sample substantially free from undesirable contaminants, which may be present therein. The components of the processed sample are passed through chromatographic means such as nanocolumns or microcolumns comprising reverse phase sorbents, for example, to separate the biomarkers into discrete particles according to size, charge, solubility, and the like. The separated biomarkers are introduced on-line into a nanospray or microspray ionization source where they are ionized and dispatched to a mass spectrometer to acquire the corresponding mass spectral profile or data. The apparatus of the present invention is adapted for carrying out all of the above steps in a continuous manner while requiring minimal human intervention or supervision. More specifically, the apparatus of the present invention is adapted to automatically process, clean and analyze a sample suspected of containing one or more biological agents though sample ionization for mass spectrometry.

In one embodiment of the apparatus of the present invention, a sample comprising centrifuged cell lysate is injected and loaded into a cartridge adapted for trapping proteins to isolate the protein biomarkers from the undesirable contaminants. The trapped proteins are then described onto a nano reverse phase HPLC column followed by separation of the mixture through liquid chromatography. The separated components are then introduced into a nanospray source of the ESI instrument for subsequent analysis in the mass spectrometer. Alternatively, the sample is desorbed from the protein-trapping cartridge through a cartridge containing a protease such as trypsin to promote proteolytic digestion of proteins to yield peptide fragments. The resulting peptide fragments are then further cleaned and concentrated to remove ionizable impurities, salts, detergents, buffers, and the like, separated by the chromatographic means, and analyzed by a tandem mass spectrometer to obtain the molecular mass and peptide sequencing information of the corresponding protein biomarkers released. Each of the sample processing components of the present invention is fluidly connected to one another through fluid conveying lines and switched by multi-port valve units for permitting passage of the sample to each component.

The apparatus of the present invention further includes a controller system in the form of a central processing unit capable of being programmed to send control signals to each of the corresponding switch valve units of the system for carrying out the steps of the present invention. The central processing unit may be programmed to control the entire process of the present invention including initiating the mass spectrometric data acquisition. The controller actuated switch valve units toggle between on and off states to direct passage of the sample in a time dependent operation as will be described hereinafter. In one mode, the controller system is adapted to initiate the steps of sample processing, including the optional step of proteolytic digestion, and mass spectrometric measurement by allowing passage of the sample from one processing component to another at specific preprogrammed time intervals.

Figure 1:
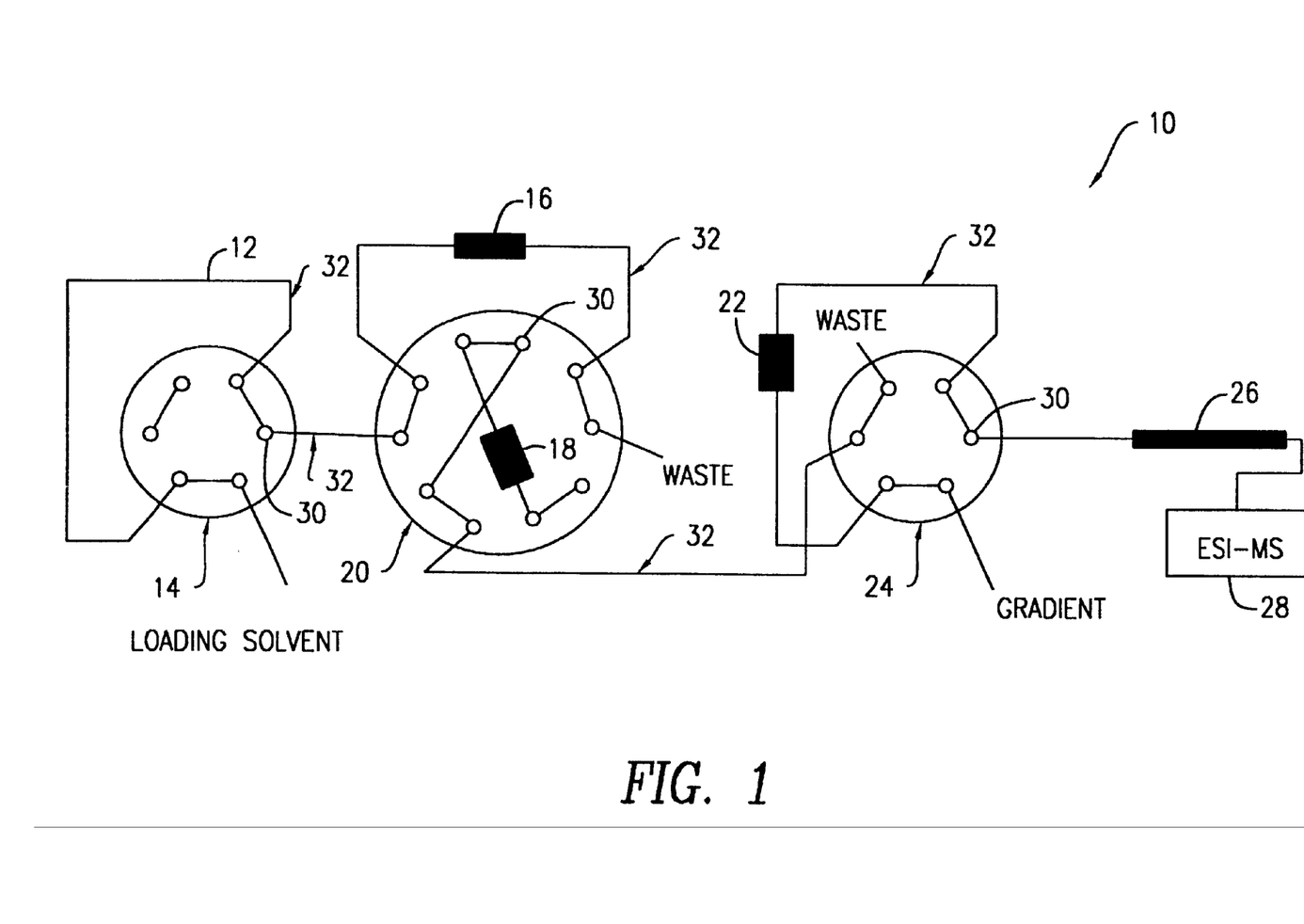
FIG. 1 is a schematic diagram of one embodiment of an apparatus of the present invention for rapidly processing and identifying biological agents in a sample.

Referring to FIG. 1, an apparatus 10 generally comprises a sample loop 12 supported by a six port switch valve unit 14, a cleanup and concentration column 16 and optionally, a proteolytic digestion column 18 supported by a ten port switch valve unit 20, a cleanup and concentration column 22 supported by a six port switch valve unit 24, a chromatographic separation column 26, and an ionization source-mass spectrometry (ESI-MS) apparatus 28. The switch valve units (14, 20, and 24) are fluid management devices with multiple inlet and outlet ports for enabling attachment of fluid tubing lines, and functions as a central switching junction for the control, direction and passage of fluid samples through corresponding components connected thereto, thus facilitating automated sample processing under the direction of a centralized preprogrammed controller. Each of the components is fluidly coupled in a linear relationship through fluid conveying lines 32 and corresponding ports 30 of the switch valve units 14, 20, and 24. The apparatus 10 further includes a programmable controller (not shown) adapted for operative engagement with the switch valve units 14, 20, and 24 to initiate the passage of the sample into each of the sample processing components 16, 18, 22, and 26, and the ESI-MS apparatus 28. Such actuation may be initiated in a time dependent manner.

The apparatus 10 may be constructed from commercially available components, as modified per applicants instructions, such as the SWITCHOS™ Advance Micro Column Switching Unit (Part No. Sw-02) for providing the column switching operations, ULTIMATE™ Fully Integrated Capillary- and Nano-HPLC System (Part No. 160003) for providing the microcolumn flow and separation processing, and FAMOS™ Wellplate Micro Autosampler (Part No. 160516) for providing routine automated sample loop injection and electronic coordination of the valve switching. Each of the components may be controlled and programmed through the UltiChrom™ software program (Part No. 160009) for configuring instrument settings and running sequences. The software program is executable on Windows 95/98 and NT based operating systems using a conventional personal computer interfaced with the above components. All the above-mentioned components and software are commercially available from LC Packings—A Dionex Company (Amsterdam, The Netherlands).

Referring back to FIG. 1, the sample is injected into the sample loop 12 from a syringe (not shown). A sample loading solvent is simultaneously pumped at a fixed rate of from about 50 to 100 $\mu$l/min to transfer the sample from the sample loop 12 into the clean up and concentration column 16 to remove non-ionic detergent and/or buffer residues and reduce the volume of the sample. The sample loading solvent may be comprised of 5% acetonitrile in 50 mM ammonium carbonate (pH 8.0). The concentration column 16 may be comprised of suitable ion exchange resins (mixture of anionic and cationic exchange resins). Suitable columns include MonoS/MonoQ 1:1, 0.5 mm I.D., 15 mm. The column 16 slows the flow of the protein biomarkers in the sample passing therethrough. The first segment of the effluent exiting from the column 16 contains the non-ionic detergent contaminants and is passed into a waste reservoir. At a preset time interval, the controller actuates the switch valve unit 20 to route the second segment of the effluent containing the protein biomarkers exiting from the column 16 to the proteolytic digestion column 18 while bypassing the waste reservoir.

The effluent containing the protein biomarkers is passed through the proteolytic digestion column 18 at a rate of from about 6 to 10 μl/min to promote the cleavage of the protein biomarkers into smaller peptide fragments. The proteolytic digestion column 18 is used in combination with a tandem mass spectrometer for peptide sequencing analysis. Suitable proteolytic digestion columns 18 may include Porozyme cartridges (0.3 mm I.D., 5 mm, 10 μm) available from Applied Biosystem (Framingham, Mass.). The switch valve unit 24 is actuated to pass the resulting effluent into the cleanup and concentration column 22 for removal of contaminants and concentration. The column 22 may include microcolumns containing uniform, stacked or mixed beds of ultrafiltration beads, reverse phase, and hydrophilic absorbents, ion exchange resins, mixed phases containing porous C4 and C8 sorbents, stacked phases containing anionic exchange resin and C8 packing, mixture of anionic and cationic exchange resins, and the like or combinations thereof. A suitable cleanup and concentration column 22 may include 300 μm I.D. Capillary Columns (5 mm, 300 Å) containing $C_{18}$ sorbents. The adsorbed peptide fragments are passed into the chromatographic separation column 26 at a rate of about 0.15 μl/min and separated by a gradient solvent. The chromatographic separation column 26 may suitably include a chromatographic column (75 μm I.D., 5 cm, 300 Å, 5 μm) containing a reverse phase $C_{18}$ sorbent. The separated peptide fragments of the protein biomarkers are then passed into the ESI-MS apparatus 28. Preferably, the mass spectrometer is a tandem mass spectrometer (MS/MS). During passage of the peptide fragments into the ESI-MS/MS apparatus 28, the switch valve unit 20 is actuated to pass a 0.1 sodium chloride solution into the cleanup and concentration column 16 and a 1:1 mixture of ammonium carbonate buffer:acetonitrile into the proteolytic digestion column 18 for washing and preconditioning in preparation of the next sample. The corresponding washing solutions are passed into the waste reservoir.

The peptide fragments may be introduced into the ESI-MS apparatus 28 by a built-in syringe pump available from Thermo-Finnigan (San Jose, Calif.) or a liquid chromatographic column. The flow rate from the syringe pump is preferably maintained from about 0.5 to 1.0 μl/min and the flow rate from the LC column is preferably maintained from about 100 to 150 nl/min. The peptide fragments are ionized using a nanospray voltage of about 2.5 kV and a heated capillary tube temperature of about 180° C. The nanospray source preferably comprises a fused silica nanospray needle available from New Objective (Woburn, Wash.). The fused silica capillary tubing is available from Polymicro Technologies (Phoenix, Ariz.). Ionized peptide fragments are passed through the heated capillary tube for desolvation. One commercially available mass spectrometer is an LCQ-Classic ion trap tandem mass spectrometer manufactured by Thermo-Finnigan (San Jose, Calif.) operated by Tune-Plus window program.

The ESI-MS/MS apparatus 28 can be adapted for activation upon a closure of a contact in the sample processor component of the apparatus 10. The mass spectral data are analyzed with MS software such as BIOWORKS or SEQUEST both available from Thermo-Finnigan (San Jose, Calif.) to obtain molecular masses of the bacterial proteins and derive mass spectral profiles of the biomarkers for the corresponding biological agent present in the sample.

Figure 2:
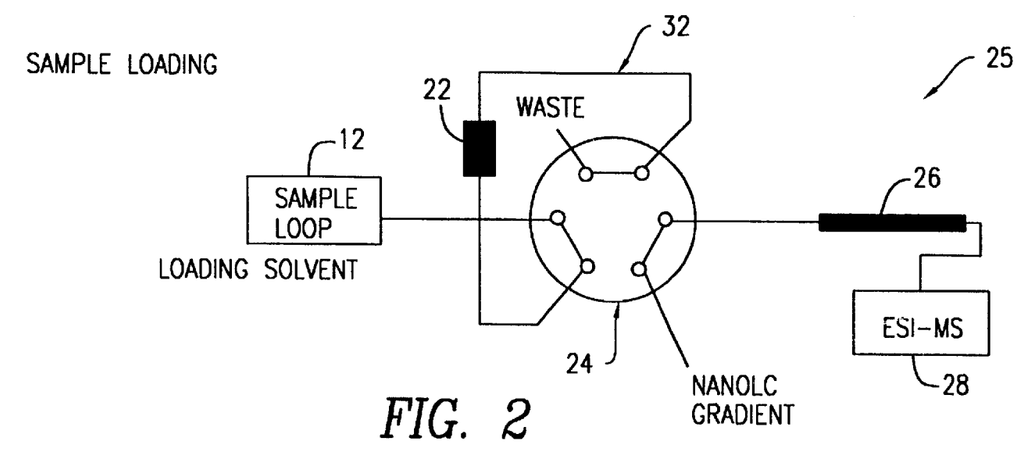
FIG. 2 is a schematic diagram of a second embodiment of an apparatus functioning in the sample loading state for rapidly processing and identifying biological agents in a sample in accordance with the present invention.

Referring to FIG. 2, an apparatus 40 for a third embodiment of the present invention is shown. The apparatus 25 includes the sample loop 12, the cleanup and concentration column 22 arranged on the switch valve unit 24, the chromatographic separation column 26, and the ESI-MS apparatus 28. The apparatus 25 is similar in all aspects to the previous embodiment except for the absence of the cleanup and concentration column 16 and the proteolytic digestion column 18. The apparatus 25 is typically used for measuring the masses of the biomarkers of the biological agents in the sample.

With specific reference to FIG. 2, the sample is injected into the sample loop 12 from a syringe (not shown). A sample loading solvent is simultaneously pumped at a fixed rate of from about 50 to 100 μl/min to transfer the sample from the sample loop 12 into the cleanup and concentration column 22 to remove detergent and/or buffer residues. The cleanup and concentration column 22 may be comprised of microcolumns containing uniform, stacked or mixed beds of ultrafiltration beads, reverse phase, and hydrophilic absorbents, ion exchange resins, mixed phases containing porous C4 and C8 sorbents, stacked phases containing anionic exchange resin and C8 packing, mixture of anionic and cationic exchange resins, and the like and combinations thereof. Suitable commercially available columns include those marketed under CAPTRAP™ (0.5×2.0 mm) capillary cartridges from Michrom (Auburn, Calif.) and 300 μm I.D. Capillary Columns-$C_8$ cartridges from LC Packings (Amsterdam, The Netherlands).

Figure 3:
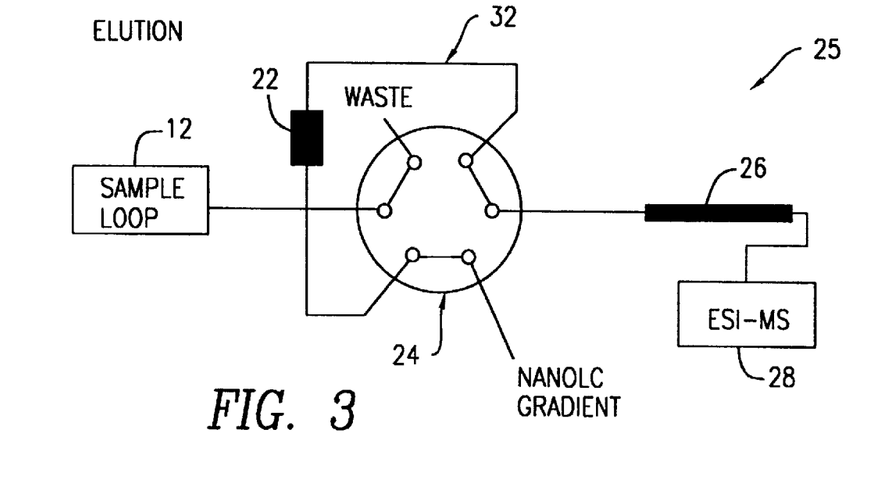
FIG. 3 is a schematic diagram of the apparatus of FIG. 2 functioning in the elution state.

The switch valve unit 24 is initially toggled to pass the sample from the sample loop 12 to the cleanup and concentration column 22. The outlet of the column 22 empties into the waste reservoir where the contaminants are discarded. After a preset time interval the switch valve unit 24 is actuated into the configuration shown in FIG. 3. In this state, the sample loop 12 is washed with a washing solvent in preparation for the next sample. The washing solvent is discarded in the waste reservoir. The gradient is passed into the cleanup and concentration column 22 to desorb the trapped bacterial proteins into the chromatographic separation column 26 at a rate of about 0.15 μl/min and separated by a gradient solvent. The chromatographic separation column 26 may suitably include a chromatographic column (75 μm I.D., 5 cm, 300 Å, 5 μm) containing reverse phase $C_8$ sorbent. The gradient is passed through the chromatographic separation column 26 for a time after total elution of the bacterial proteins to wash and precondition the cleanup and concentration column 22 and the chromatographic column 26 for the next sample. The eluted bacterial protein components are then introduced to the ESI-MS apparatus 28 for mass spectrometric analysis as described above.

Figure 4:
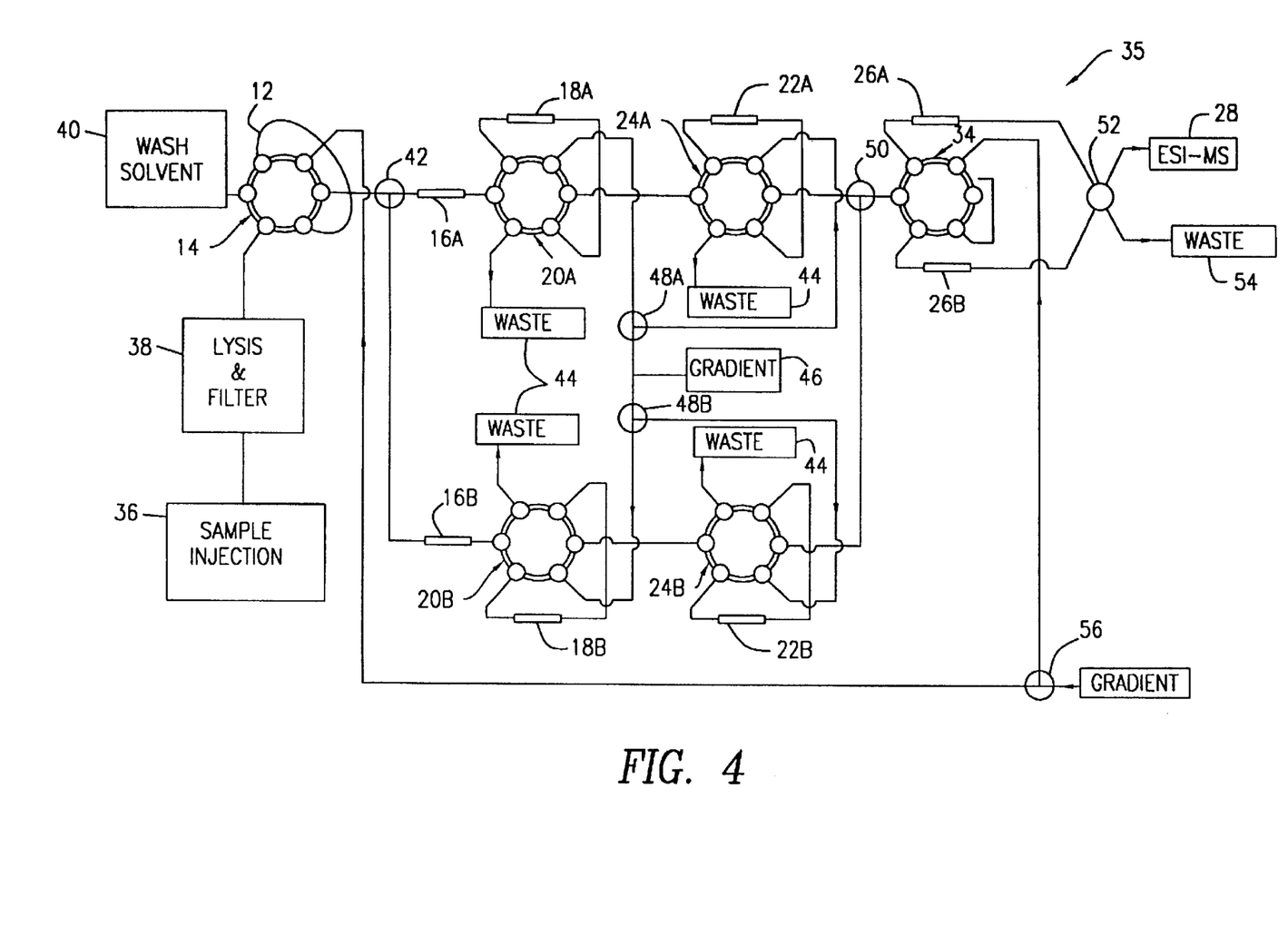
FIG. 4 is a schematic diagram of a third embodiment of an apparatus for rapidly processing and identifying biological agents in a sample in accordance with the present invention.

Referring to FIG. 4, the apparatus 35 includes a multiple sample processing configuration for facilitating continuous operation. The apparatus 35 is similar in all aspects as to the apparatus 10. The use of multiple parallel in-line processing components allows the apparatus 35 to rapidly identify samples with minimal delay due to the sample processing step. The apparatus 35 includes the sample loop 12 supported by the switch valve unit 14, the cleanup and concentration column 16A and the proteolytic digestion column 18A supported by the switch valve unit 20A, the cleanup and concentration column 22A supported by the switch valve unit 24A, the chromatographic separation columns 26A and 26B supported by a multiple port switch valve unit 34, and the ionization source-mass spectrometry (ESI-MS) apparatus 28.

The apparatus 35 further includes a separate parallel processing line comprising the cleanup and concentration column 16B and the proteolytic digestion column 18B supported by the switch valve unit 20B, the cleanup and concentration column 22B supported by the switch valve unit 24B. The number of parallel processing line is not limited to two, and may include configurations having more than two processing lines for providing increased sample processing efficiency.

The apparatus 35 further includes an autosampler device 36, an ultrasonic disrupter and filter device 38, a wash solvent supply 40, a switch valve 42, a waste reservoir 44 connected to each of the switch valve units 20A, 20B, 24A and 24B, a gradient supply 46 connected to each of the switch valve units 20A, 20B, 24A and 24B regulated by switch valves 48A and 48B, a switch valve 50 connecting between the switch valve units 24A and 24B to the switch valve unit 34, a switch valve 52 connecting between the switch valve unit 34 and the ESI-MS apparatus 28 and a waste reservoir 54. Additionally, a gradient pump 56 for supplying gradient is connected to the switch valve units 14 and 34.

The autosample device 36 introduces a sample suspected of containing biological agents to the ultrasonic disrupter and filter device 38 for mechanically and/or chemically disrupting the cellular bacteria and filtering the insoluble debris to yield a supernatant. The supernatant is injected into the sample loop 12 where it is transferred along with the gradient by the switch valve unit 14 to the switch valve 42 which directs the sample to one of the dual sample processing lines for processing through the cleanup and concentration column 16A or 16B and the proteolytic digestion column 18A or 16B supported by the switch valve unit 20A or 20B, the cleanup and concentration column 22A or 22B supported by the switch valve unit 24A or 24B as described in FIG. 1. The wash solvent supply 40 furnishes a wash solvent to each of the switch valve units 14, 20, and 24 for enabling washing and preconditioning of each of the components supported thereon before receiving the next sample for processing. The gradient supply 46 provides the gradient flow to each of the processing components through switch valves 48A and 48B, and the waste reservoirs 44 receive and collecting the waste flow therefrom. The sample containing biomarkers that are proteolytically digested, purified and concentrated, is transferred to the switch valve 50 for introduction into the switch valve unit 34. The switch valve unit 34 transfers the sample to one of the chromatographic separation columns 26A or 26B for separating the components of the peptide fragments.

Figure 5:
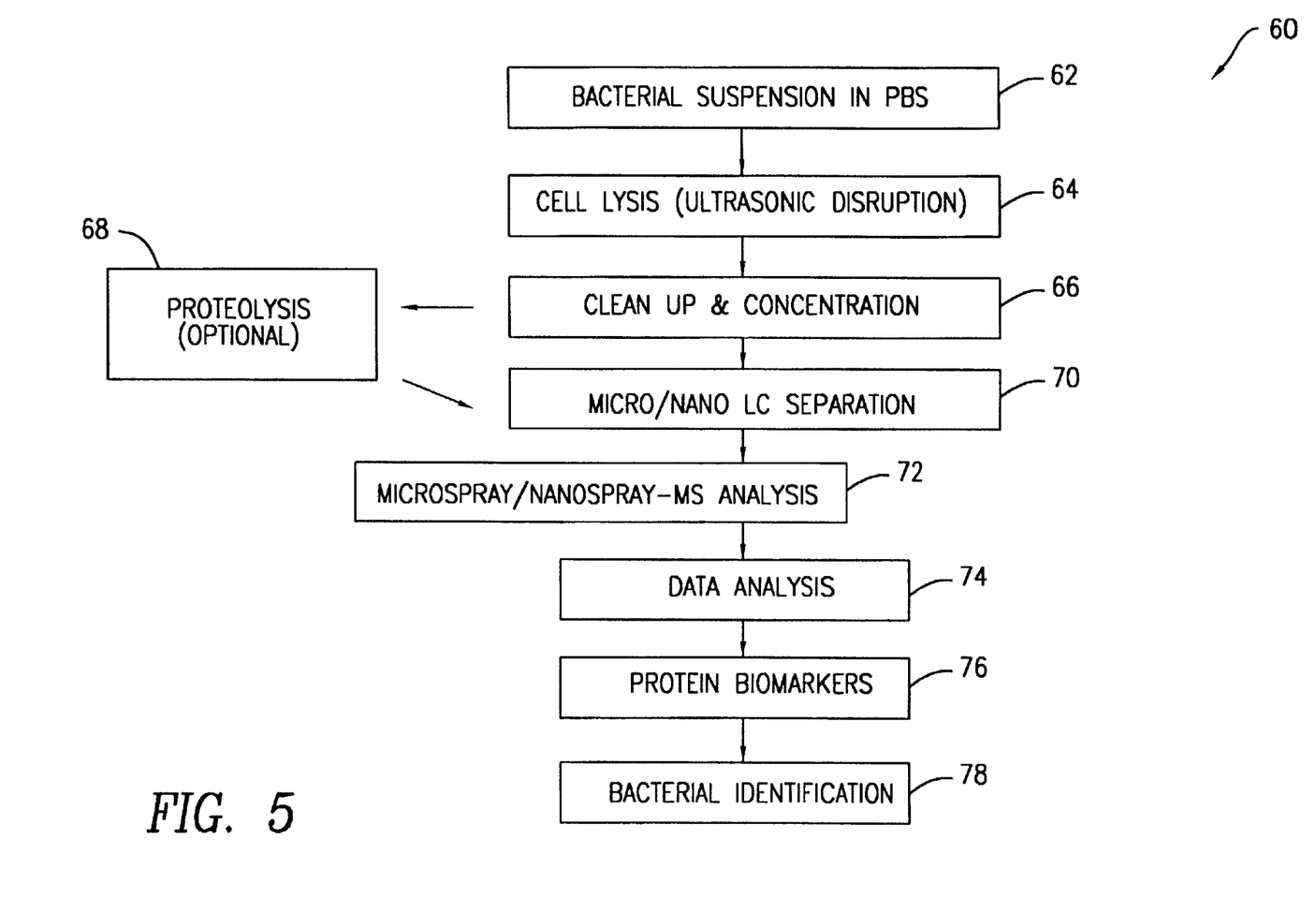
FIG. 5 is a flow chart illustrating the steps carried out by the apparatus of FIG. 4 in accordance with the present invention.

Referring to FIG. 5, a flowchart 60 shows the steps programmed into the controller (not shown) for performing the method of the present invention. In step 62, the controller initiates introduction of a bacterial sample in the form of a suspension through the actuation of the sample injector 36 to place the sample into the ultrasonic disrupter and filter device 38. Once the sample is loaded into the ultrasonic disrupter and filter device 38, the controller proceeds to step 64 to initiate the cell lysis of the bacterial sample by activating the ultrasonic disrupter and filter device 38. During step 64, the bacterial cells are subjected to ultrasonic energy, which disrupts the cells in a manner sufficient to release biomarkers from the cells. Upon completion of cell lysis, the sample is centrifuged to concentrate the cellular debris and other particulates and passed through a filter media (not shown) to isolate the supernatant containing the desired biomarkers. The supernatant is injected into the sample loop 12 for transfer to the switch valve 42 through the switch valve unit 14.

Upon completion of step 64, the controller initiates step 66 whereby the supernatant containing the protein biomarkers are transferred to the cleanup and concentration columns 16A or 16B to remove nonionized detergent residues, buffers, salts and ionizable impurities. The controller initiates optional step 68 whereby the purified and concentrated supernatant is loaded through the switch valve units 20A or 20B for passage through the proteolytic digestion columns 18A or 18B to cleave the intact protein biomarkers into peptide fragments. The supernatant is loaded into the cleanup and concentration column 22A or 22B through switch valve unit 24A or 24B to remove salts and buffer remaining.

The controller initiates step 70 by passing the elution through the chromatographic separation column 26A or 26B to separate the individual biomarkers. The controller then initiates step 72 whereby the separated biomarkers are introduced into the nanospray ionization source for ionizing the biomarkers prior to introduction into the mass spectrometer. It is noted that steps 62 through 72 can be carried out through sequences preprogrammed into the controller using commercially available software such as Utichrom™ software available. from LCPackings of Amsterdam, the Netherlands.

As the biomarkers are ionized by the nanospray source, the controller initiates the mass spectrometer for data acquisition and analysis in step 74. The controller through preprogrammed sequences may trigger the operation of the mass spectrometer by sensing a contact closure in the sample processing portion of the apparatus 35. Optionally, the mass spectrometer can be operated manually through the use of commercially available software such as Tune-Plus window software from Thermo-Finnigan, San Jose, Calif.

The data acquired by the mass spectrometer is analyzed using suitable commercially available mass spectrometry software such as Bioworks from Thermo-Finnigan or MoWed from Dr. Terry Lee, of City of Hope, Duarte, Calif., to arrive at the molecular mass readings of the bacterial proteins and/or to derive the peptide sequencings of the bacterial proteins for identification in step 76. The bacteria linked to the protein biomarkers are then identified in step 78.

The foregoing discussion discloses and describes merely exemplary embodiments of the present invention. One skilled in the art will readily recognize from such discussion, and from the accompanying drawings, examples and claims, that various changes, modifications and variations can be made therein without departing from the spirit and scope of the invention as defined in the following claims.

EXAMPLE 1

Sample Preparation for MS Analysis

Bacteria

A number of pathogenic bacteria including *Bacillus anthracis, Brucella melitensis, Francisella tularrensis,* and *Yirsinia pestis,* and nonpathogenic bacteria including *Bacillus cereus, Bacillus subtilis, Bacillis thuringiensis,* and *Erwinia herbicola,* were analyzed and each are of different genera, species, and strains. The pathogenic bacteria strains γ-radiated and lyophilized by the U.S. Army Laboratories at Dugway Proving Ground, UT, and Aberdeen Proving Ground, MD. Nonpathogenic bacteria cells of different strains were grown in-house by incubating for 24 hours at 37° C. on trypticase soy agar or nutrient agar plates, harvested and lyophilized.

Cell Lysis

Lyophilized bacteria cells (0.1 mg; $10^9$ cells/mg) were suspended in 200 $\mu$l of a solution containing a solvent containing 0.1% trifluoroacetic acid (TFA), 0.1% formic acid, and 0.05% Triton-X in 50 mM PBS. The suspended cells were sonicated using the Ultrasonic Sonifier 250 from Branson (Danbury, Conn.) and the Ultrasonic Sonter from Parkell (Farmingdale, N.Y.) for thirty seconds. The resulting cell lysate was centrifuged to settle the cellular debris and other particulates and the supernatant was extracted for further investigation.

EXAMPLE 2

Sample Clean Up and Concentration for ESI-MS Analysis

An automated biological sample processor of the present invention, was built according to the schematic of FIG. 1 by LCPackings (Amsterdam, The Netherlands). The processor includes an autosampler with two-six-port valves and a nano-LC system. The processor was adapted to operate in two modes: 1) sample processing of intact bacterial proteins, and 2) on-line proteolytic digestion of the intact bacterial protein for peptide sequencing analysis. In both modes, the processor was programmed to conduct each process automatically.

The cell lysate (50–100 µl) prepared in Example 1 was drawn into a 100 µl syringe and injected into a sample loop (100 µl). 400 µl of a sample loading solution comprising 0.5% TFA/5.0% acetonitrile in water, was pumped at a rate of 50–100 µl/min to transfer the sample from the sample loop into a cleanup and concentration cartridge (CapTrap, 0.5×2.0 mm, from Michrom of Auburn, Calif., or alternatively, $C_8$ cartridge, 300 µm ID, 5 mm, 300 Å from LCPackings of Amsterdam, The Netherlands) to wash off any remnants of detergent and/or buffers from the cell lysate.

The remaining trapped bacterial protein was desorbed from the cleanup and concentration cartridge by passing a gradient flow therethough into a reverse-phase $C_8$ nano-column (75 µm ID, 5 cm, 5 µm) to separate the components. A first solvent referred herein as Solvent A was comprised of 0.1% formic acid/5% aqueous acetonitrile) and a second solvent referred herein as Solvent B was comprised of 0.1% formic acid/100% acetonitrile were combined to form the gradient flow. Initially, the gradient flow comprised 20–30% of the solvent B, which changed to 100% of the solvent B over a 10 minute period and maintaining the 100% of the solvent B for 7 minutes before changing back to 20–30% of the solvent B and maintained for another 3 minutes. The total time for separation of the bacterial protein from the residual detergent and buffer took about 20 min. It is noted that the bacterial protein was eluted from the nano column in about 12 min, however, the gradient flow was maintained longer to ensure total elution and preparation of the cartridge for the next sample.

The eluted component comprising the bacterial protein was introduced into a nanospray ionization source through a fused silica nanospray needle from New Objective (Woburn, Mass.) for mass spectrometric analysis using an LCQ-Classic ion trap tandem mass spectrometer from Thermo-Finnigan (San Jose, Calif.).

Mass Spectral Analysis

The sample was either infused using a built-in syringe pump (Thermo-Finnigan) or from a liquid chromatography (LC) column. The flow rate for infusion experiments was maintained at about 0.5–1.0 µl/min and the LC flow rate for nanospray experiments was maintained at 100–150 nl/min. The nanospray experiments were conducted with the instrument operating at a nanospray voltage at 2.5 kV and the heated micro capillary tube temperature at about 180° C.

The mass spectrometer was operated manually in TUNE-PLUS window during the infusion experiments. Alternatively, preprogrammed MS sequences were loaded and the data acquisition was triggered by contact closure from the sample processor. Automated gain was kept at $5\times10^7$ and the injection parameters such as microscan count and maximum injection time were maintained during LC/MS experiments at 3–5 and 200, respectively. The acquired data was analyzed either by Bioworks (Thermo-Finnigan) or by MoWed program to obtain the molecular mass of the bacterial proteins and to derive biomarkers for each individual bacterium present in the sample.

EXAMPLE 3

Sample Clean Up and Concentration with Proteolysis of Bacterial Proteins for ESI-MS Analysis For analysis of bacterial protein extracts for peptide sequencing, the sample prepared in Example 1 was loaded into an ion-exchange precolumn (MonoS/MonoQ, 1:1, 0.5 mm ID, 15 mm) with 5% acetonitrile in 50 mM ammonium carbonate (pH 8.0) at a rate of 100 µl/min for preconcentration and removal of non-ionic detergents. 100 µl of 1M sodium chloride in ammonium carbonate buffer was injected. The effluent was then passed though a cartridge impregnated with a protease [i.e. trypsin (Porozyme cartridge, 0.3 mm ID, 5 mm, 10 µm, from Applied Biosystems of Framingham, Mass.)] at a rate of about 6 µl/min and at a temperature of about 45° C. for at least 4 minutes. The eluent was then passed through a cleanup/concentration cartridge ($C_{18}$ cartridge, 300 µm ID, 5 mm, 300 Å) where any remnants of detergent and/or buffers are washed from the eluent.

The adsorbed peptides were eluted into a reverse phase $C_{18}$ column (75 µm ID, 5 cm, 300 Å, 5 µm) at a rate of 0.15 µl/min and separated by gradient elution comprising 20–95% of the solvent A and 5% acetonitrile in 0.1% formic acid in water, and the solvent B and 0.1% formic acid in 80% acetonitrile in water, for about 10 minutes. The peptides were passed through a tandem mass spectrometer to generate a mass spectral profile of the sample. During the analysis, the ion-exchange and Porozyme cartridge were washed with 0.1 M sodium chloride solution and a 1:1 mixture of ammonium carbonate buffer:acetonitrile, respectively, for the next sample.

The mass of the peptide biomarkers was obtained by analysis of the data and the corresponding amino acid sequence of the peptides. The tandem mass spectrometric data of the peptides was analyzed by "SEQUEST" software to obtain sequence information and the identification of the bacterial protein biomarkers from available protein databases. Details on operation of the SEQUEST software may be further established in J. Eng et al., "An Approach to Correlate Tandem Mass Spectral Data of Peptides with Amino Acid Sequences in a Protein Database", J. Am. Soc. Mass Spectrom., 5, 976–989, 1995.

What is claimed is:

1. An apparatus for rapidly identifying biological agents in a sample suspected of containing the same, said apparatus comprising:

releasing means for releasing biomarkers from the biological agents in the sample;

at least one sample processing module fluidly connected to the releasing means, said at least one sample processing module including a cleanup and concentration column for separating the contaminants from the biomarkers contained in the sample and concentrating the volume of the sample;

an ionization source fluidly connected to said at least one sample processing module, for ionizing the biomarkers and forming a stream of ionized biomarkers;

a detector for analyzing the stream of ionized biomarkers to obtain at least one parameter of the ionized biomarkers indicative of the identity of the biological agent; and a controller operatively connected to the releasing means, the sample processing module, the separation module, the ionization source and the detector to provide programmed coordination of said components for orderly passage of the sample therethrough.

2. The apparatus of claim 1 further comprising a separation module fluidly connected to an outlet of each of the at least one sample processing module, said separation module including at least one chromatographic separation column for separating the biomarkers into discrete particles.

3. The apparatus of claim 1 wherein the biomarkers are proteins.

4. The apparatus of claim 3 wherein the sample processing module further comprises a proteolytic digestion column fluidly connected between the releasing means and the cleanup and concentration column, for facilitating enzymatic cleavage of the protein biomakers into peptide fragments.

5. The apparatus of claim 4 wherein the sample processing module further comprises a second cleanup and concentration column fluidly connected between the releasing means and the proteolytic digestion column.

6. The apparatus of claim 5 wherein the second cleanup and concentration column comprises an ion exchange resin.

7. The apparatus of claim 4 wherein the proteolytic digestion column includes a protease.

8. The apparatus of claim 7 wherein the protease is trypsin.

9. The apparatus of claim 1 wherein the detector is a mass spectrometer.

10. The apparatus of claim 9 wherein the mass spectrometer is a tandem mass spectrometer.

11. The apparatus of claim 1 wherein the at least one sample processing module is a plurality of the sample processing modules arranged in a parallel relationship to one another.

12. The apparatus of claim 1 wherein the releasing means further comprises an ultrasound generating assembly providing sufficient ultrasonic energy to disrupt the biological agent and release a biomarker therefrom.

13. The apparatus of claim 12 wherein the releasing means further comprises a centrifuge for facilitating release of the biomarkers from the biological agents.

14. The apparatus of claim 13 wherein the releasing means further comprises a filter for facilitating release of the biomarkers from the biological agents.

15. The apparatus of claim 1 wherein the at least one sample processing module is supported on a switch valve unit.

16. The apparatus of claim 15 wherein the controller is connected to the switch valve unit for controlling the passage of the sample through the at least one sample processing module.

17. The apparatus of claim 2 wherein the at least one sample processing module and the separation module are each supported on a switch valve unit.

18. The apparatus of claim 17 wherein the controller is connected to the switch valve unit for controlling the passage of the sample through the at least one sample processing module and the separation module.

19. The apparatus of claim 2 further comprising a wash solvent supply source fluidly connected to the releasing means, the at least one sample processing module and the separation module for facilitating washing thereof between passage of samples therethrough.

20. The apparatus of claim 2 further comprising a gradient supply source fluidly connected to the at least one sample processing module and the separation module for facilitating passage of the sample therethrough.

21. The apparatus of claim 2 further comprising a waste reservoir fluidly connected the at least one sample processing module and the separation module for collecting contaminants removed from the sample.

22. The apparatus of claim 1 wherein the contaminant is selected from the group consisting of detergents, salts, buffers, ionizable impurities, and combinations thereof.

23. The apparatus of claim 1 wherein the ionization source is selected from the group consisting of a matrix-assisted laser desorption/ionization assembly and an electrospray ionization assembly.

24. The apparatus of claim 1 wherein the cleanup and concentration column comprises a media selected from the group consisting of uniform, stacked or mixed beds of ultrafiltration beads, ion exchange resins, gel filtration substrates, reverse phase and hydrophilic absorbents, ion exchange resins, mixed phases containing porous C2, C4 and C8 sorbents, stacked phases containing anionic exchange resin and C8 packing, mixture of anionic and cationic exchange resins, and combinations thereof.

25. The apparatus of claim 1 wherein the at least one chromatographic separation column is selected from the group consisting of a reverse phase C8 nanocolumn and a reverse phase C18 column.

26. The apparatus of claim 1 wherein the at least one parameter is the mass of the ionized biomarkers.

27. The apparatus of claim 26 wherein the detector is further adapted for generating a mass spectral profile of the biomarkers in the sample.

28. The apparatus of claim 27 further comprising a mass spectral profile matching device including a database for storing a library of mass spectral profiles of biomarkers from known biological agents, said matching device being adapted to analyze the mass spectral profile generated by the detector against the mass spectral profile library to make a positive identification.

29. An apparatus for rapidly identifying biological agents in a sample suspected of containing the same, said apparatus comprising:

releasing means for releasing biomarkers from the biological agent present in a sample;

at least one sample processing module including a cleanup and concentration column for removing contaminants and concentration the released biomarkers in the sample;

a biomarker separation module including a chromatographic separation column for separating the biomarkers into discrete particles;

an ionization assembly for ionizing the biomarkers and forming a stream of ionized biomarkers;

a detector for analyzing the stream of ionized biomarkers to obtain at least one parameter of the ionized biomarkers; and a controller operatively connected to the releasing means, the at least one sample processing module, the biomarker separation module, the ionization assembly, and the detector, to provide programmed operation instructions to the same.

30. The apparatus of claim 29 wherein the parameter is mass of the ionized biomarkers.

31. The apparatus of claim 29 further comprising a library of biomarkers from biological agents having specified masses wherein the mass of the ionized biomarkers is compared with the library of biomarkers to identify the biological agent in the sample.

32. The apparatus of claim 29 wherein the releasing means comprises an ultrasound generating assembly for providing sufficient ultrasonic energy to disrupt the biological agent and release a biomarker therefrom.

33. The apparatus of claim 29 wherein the biomarker separation module comprises a liquid chromatographic column.

* * * * *